US009442066B2

(12) United States Patent
Tekin et al.

(10) Patent No.: US 9,442,066 B2
(45) Date of Patent: Sep. 13, 2016

(54) TRAVELING WAVE BASED THZ SIGNAL GENERATION SYSTEM AND METHOD THEREOF

(71) Applicants: Ahmet Tekin, Irvine, CA (US); Ahmed Emira, Irvine, CA (US); Suat Utku Ay, Pullman, WA (US)

(72) Inventors: Ahmet Tekin, Irvine, CA (US); Ahmed Emira, Irvine, CA (US); Suat Utku Ay, Pullman, WA (US)

(73) Assignee: WAVE WORKS, INC., Irvine, CA (US)

( * ) Notice: Subject to any disclaimer, the term of this patent is extended or adjusted under 35 U.S.C. 154(b) by 0 days.

(21) Appl. No.: 14/505,951

(22) Filed: Oct. 3, 2014

(65) Prior Publication Data

US 2016/0097718 A1    Apr. 7, 2016

(51) Int. Cl.
*G01D 18/00* (2006.01)
*G01N 21/55* (2014.01)

(52) U.S. Cl.
CPC ......... *G01N 21/55* (2013.01); *G01N 2201/061* (2013.01)

(58) Field of Classification Search
CPC ........... G01N 21/55; G01N 2201/061; H03B 2200/0084; H03K 3/0315; H04B 1/38; H04B 10/00; H04B 10/90
USPC ..................................................... 250/252.1
See application file for complete search history.

(56) References Cited

U.S. PATENT DOCUMENTS

| 2,445,348 | A | * | 7/1948 | Ford | G01R 27/06 324/646 |
|---|---|---|---|---|---|
| 4,052,673 | A | | 10/1977 | Herzog | |
| 4,400,630 | A | | 8/1983 | Owen | |
| 5,422,613 | A | | 6/1995 | Nativ | |
| 5,493,719 | A | | 2/1996 | Smith et al. | |
| 5,764,111 | A | | 6/1998 | Bushman | |
| 6,707,344 | B2 | | 3/2004 | Cargill et al. | |
| 6,864,728 | B1 | | 3/2005 | Lu et al. | |
| 7,315,678 | B2 | | 1/2008 | Siegel et al. | |
| 7,741,921 | B2 | | 6/2010 | Ismailov | |
| 8,130,049 | B2 | | 3/2012 | Huang et al. | |
| 8,310,093 | B1 | * | 11/2012 | Corum | H02J 3/18 307/43 |
| 2006/0016997 | A1 | | 1/2006 | Siegel | |
| 2007/0132489 | A1 | * | 6/2007 | Corum | H02J 3/28 327/116 |
| 2008/0137093 | A1 | | 6/2008 | Kang et al. | |
| 2008/0169859 | A1 | | 7/2008 | Garcia et al. | |
| 2012/0062286 | A1 | | 3/2012 | Ginsburg et al. | |
| 2012/0075034 | A1 | | 3/2012 | Afshari et al. | |
| 2012/0169427 | A1 | | 7/2012 | Emira et al. | |
| 2012/0212383 | A1 | * | 8/2012 | Sengupta | H01Q 9/04 343/742 |
| 2012/0251125 | A1 | * | 10/2012 | Harman | H04J 14/02 398/135 |
| 2013/0157584 | A1 | * | 6/2013 | Tekin | H03L 5/00 455/73 |
| 2014/0166868 | A1 | * | 6/2014 | Tekin | H03B 19/00 250/252.1 |

OTHER PUBLICATIONS

Floyd, et al., IEEE Journal of Solid-State Circuits, Jan. 2005, pp. 156-16.

(Continued)

*Primary Examiner* — David J Makiya
*Assistant Examiner* — Taeho Jo
(74) *Attorney, Agent, or Firm* — Oktay Enterprises Int'l, LLC; Sevgin Oktay (57) ABSTRACT

TeraHertz signal generation system based on traveling-wave oscillators providing extraction of orders of magnitude higher oscillation frequencies resulting in frequency multipliers and THz transceivers that can generate, transmit and sense THz frequency signals for sensing/imaging.

4 Claims, 8 Drawing Sheets

(56) References Cited

OTHER PUBLICATIONS

Verma, et al., IEEE Journal of Solid-State Circuits, vol. 39, No. 4, Apr. 2004, pp. 709-713.
Grayzel, et al., IEEE MTT-S International Microwave Symposium Digest, 1978, pp. 321-322.
Raisanen, et al., Microwave and Optical Technology Letters, vol. 4, No. 1, 1978, pp. 29-33.
Wilkinson, E. J., "An N-way Power Divider," Iee Trans. on Microwave Theory and Techniques, vol. 8, Jan. 1960, pp. 116-118.

* cited by examiner

TRAVELING WAVE BASED THZ SIGNAL GENERATION SYSTEM AND METHOD THEREOF

This is a division of parent application Ser. No. 13/717,489, filing date 17 Dec. 2012, "Traveling Wave Based THz Signal Generation System and Method Thereof" assigned to the same assignee as the present invention.

BACKGROUND

All references cited in this specification, and their references, are incorporated by reference herein where appropriate for teachings of additional or alternative details, features, and/or technical background. More specifically, U.S. Pat. No. 7,741,921 "Trigger-Mode Distributed Wave Oscillator" (TMDWO), US Pub. 2012/0169427, "Force-Mode Distributed Wave Oscillator and Amplifier Systems" (FMDWO), and U.S. application Ser. No. 12/374,165 "Pumped Distributed Wave Oscillator System" (PDWO) are incorporated by reference which form the core oscillators of this application.

Disclosed is a Traveling Wave Based THz Signal Generation System [TWSGS] and Method of use thereof. It is well-known that THz signals are electromagnetic waves at frequencies in the trillion ($1\times10^{12}$) cycles per second or terahertz range from 0.3 to 3 THz. The term applies to electromagnetic radiation with frequencies between the high-frequency edge of the millimeter wave band, 300 gigahertz ($3\times10^{11}$ Hz), and the low frequency edge of the far-infrared light band, 3000 GHz ($3\times10^{12}$ Hz). Corresponding wavelengths of radiation in this band range from 1 mm to 0.1 mm (or 100 µm). Because terahertz radiation begins at a wavelength of one millimeter and proceeds into shorter wavelengths, it is sometimes known as the sub-millimeter band, and its radiation as sub-millimeter waves.

Since Terahertz radiation falls in between infrared radiation and microwave radiation in the electromagnetic spectrum, it shares some properties with each of these. Like microwave radiation, terahertz radiation can penetrate a wide variety of non-conducting materials. Terahertz radiation can pass through clothing, paper, cardboard, wood, masonry, plastic and ceramics. The penetration depth is typically less than that of microwave radiation. Terahertz radiation has limited penetration through fog and clouds and cannot penetrate liquid water or metal. Like infrared and microwave radiation Terahertz radiation travels in a line of sight and is non-ionizing. Being non-ionizing, it is generally not harmful to human beings. Terahertz radiation can penetrate fabrics and plastics, so it can be used in surveillance, such as security screening, to uncover concealed weapons on a person, remotely. Other areas of promising research are medical imaging, spectroscopy in chemistry and biochemistry; potential uses in high-altitude telecommunications between aircraft and satellites avoiding the problem of terahertz signals being absorbed in the atmosphere. Other possible uses of terahertz sensing and imaging are proposed in manufacturing, quality control, and process monitoring. These in general exploit the traits of plastics and cardboard being transparent to terahertz radiation, making it possible to inspect packaged goods.

Though the potential is there for the uses of Terahertz radiation, technology for generating and manipulating it is in its infancy, and is a subject of active research. It represents the region in the electromagnetic spectrum that the frequency of electromagnetic radiation becomes too high to be measured by directly counting cycles using electronic counters, and must be measured by the proxy properties of wavelength and energy. Similarly, in this frequency range the generation and modulation of coherent electromagnetic signals ceases to be possible by the conventional electronic devices used to generate radio waves and microwaves, and requires new devices and techniques. In mid-2007, scientists at the U.S. Department of Energy's Argonne National Laboratory, along with collaborators in Turkey and Japan, announced the creation of a compact device that can lead to portable, battery-operated sources of T-rays, or terahertz radiation. (See *Science News*: "New T-ray Source Could Improve Airport Security, Cancer Detection," 27 Nov. 2007). As described in Science News, this new T-ray source uses high-temperature superconducting crystals grown at the University of Tsukuba, Japan. These crystals comprise stacks of Josephson junctions that exhibit a unique electrical property: When an external voltage is applied, an alternating current will flow back and forth across the junctions at a frequency proportional to the strength of the voltage; this phenomenon is known as the Josephson effect. These alternating currents then produce electromagnetic fields whose frequency is tuned by the applied voltage. Even a small voltage—around two millivolts per junction—can induce frequencies in the terahertz range according to the article. In 2008, engineers at Harvard University demonstrated that room temperature emission of several hundred nanowatts of coherent terahertz radiation could be achieved with a semiconductor source. THz radiation was generated by nonlinear mixing of two modes in a mid-infrared quantum cascade laser. Until then, sources had required cryogenic cooling, greatly limiting their use in everyday applications. In 2009, it was shown that T-waves are produced when unpeeling adhesive tape. The observed spectrum of this terahertz radiation exhibits a peak at 2 THz and a broader peak at 18 THz. The radiation is not polarized. The mechanism of terahertz radiation is tribocharging of the adhesive tape and subsequent discharge. ("Peeling Adhesive Tape Emits Electromagnetic Radiation At Terahertz Frequencies," www.opticsinfobase.org.) In 2011, Japanese electronic parts maker Rohm and a research team at Osaka University produced a chip capable of transmitting 1.5 Gbit/s using terahertz radiation. ("New Chip Enables Record-Breaking Wireless Data Transmission Speed," www.techcrunch.com,)

As mentioned earlier, though the potential is there for very attractive uses of Terahertz radiation, technology for generating and manipulating it is still in its infancy. There have been several approaches to achieve radiative signals in the THz levels. In its formative years, this was accomplished by using various techniques including thin-film superconductive circuitry incorporating Josephson tunnel junctions; diode based multipliers; varactor diode type multiplier by cascading diode multipliers; harmonic-mixing technique to generate high frequency oscillation signals; sub-harmonic mixing; mixing frequency multipliers; sub-harmonic mixing with Doppler effects; combining equally spaced multiple phases of a nonlinear oscillator; frequency tripler by using a three stage oscillator; ring-type phase-based oscillators; voltage controlled oscillators and combinations thereof. Nowadays, microelectronics have developed to the point where radiation within terahertz frequency can be generated and used at least by propagating a lower frequency signal to transceivers which multiply the frequency up to the desired frequency range.

An example of this "propagation" approach is described by Ginsburg, et al., in US Pub. No. 2012/0062286 entitled "Terahertz Phased Array System." Phase array systems have become commonplace, having several uses, the most common being for radar systems (i.e., pulse radar and Doppler shift radars). According to Ginsburg, Phased array radar has replaced most of the previous generations of mechanical sweep radar systems because there is a lower likelihood of failure due to wear since mechanic components are replaced with electronics and because the sweep rates are much higher.

Figure 1:
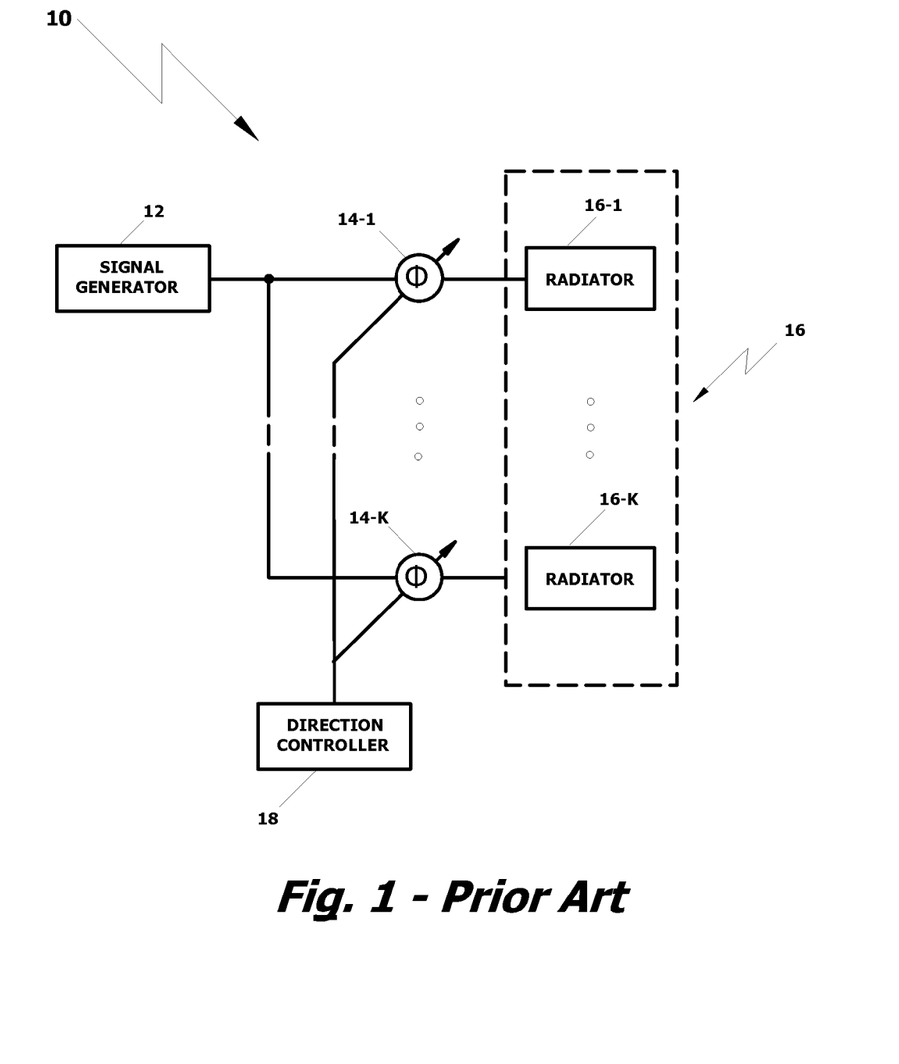
FIG. 1 shows a block diagram illustrating the basic functionality of a conventional phased array system according to prior art.

Referring now to the drawings, FIG. 1 shows a block diagram illustrating the basic functionality of a conventional phased array system 10. System 10 generally comprises a signal generator 12, phase shifters 14-1 to 14-K, a phased array 16 that includes radiators 16-1 to 16-K, and a direction controller 18. Following Ginsburg, in operation, the signal generator 12 provides a signal that is to be transmitted (i.e., pulse for a pulse radar). Based on the desired direction, the direction controller 18 provides control signals to the phase shifters 14-1 to 14-K, which varies the phase of the signal provided to each of the radiators 16-1 to 16-K within the phased array. Because the signals transmitted through radiators 16-1 through 16-K are generally out-of-phase with one another, constructive and destructive interference of the radiated signal forms a beam in a desired direction.

Ginsburg explains further that these conventional systems have been limited to conventional radio frequency (RF) frequency ranges. He cites the example that the frequency range for conventional radar is between 3 MHz (for HF-band radar) and 110 GHz (for W-band radar). The reason for the use of these relatively low frequency ranges being that there has, historically, been an unavailability of compact semiconductor sources of coherent radiation at the terahertz frequency range (which is generally between 0.1 THz and 10 THz). Generally, electronics and oscillators in the microwave range run out of power gain with increasing frequency, and typical broadband infrared blackbody sources begin losing available power within this region. Use of terahertz radiation, however, is highly desirable because of its unique properties. Namely, terahertz radiation has properties of lower frequency radiation (i.e., microwaves) which can be generated electrically and higher frequency radiation (i.e., visible light) which can be controlled using optics.

Ginsburg goes on to explain that today there exists two general types of terahertz sources: incoherent source and coherent sources. The incoherent sources are generally broadband incoherent thermal sources, which includes ultra-short femtosecond pulsed laser exciting photo conductive antennas, nonlinear electro-optical crystals, or non-linear transmission lines that suffers from very poor conversion efficiency (1 W laser pulse produces broadband energy in the nW-mW range). The coherent sources are generally narrow-band continuous wave (CW) coherent sources which include diode multiplying microwave oscillators, gas lasers using carbon dioxide laser pumping methanol or cyanic acid, optical down conversion by difference mixing, and semiconductor quantum lasing. These coherent sources, though, generally consume a large amount of power, are not compact, require exotic materials, and/or are expensive.

Figure 2:
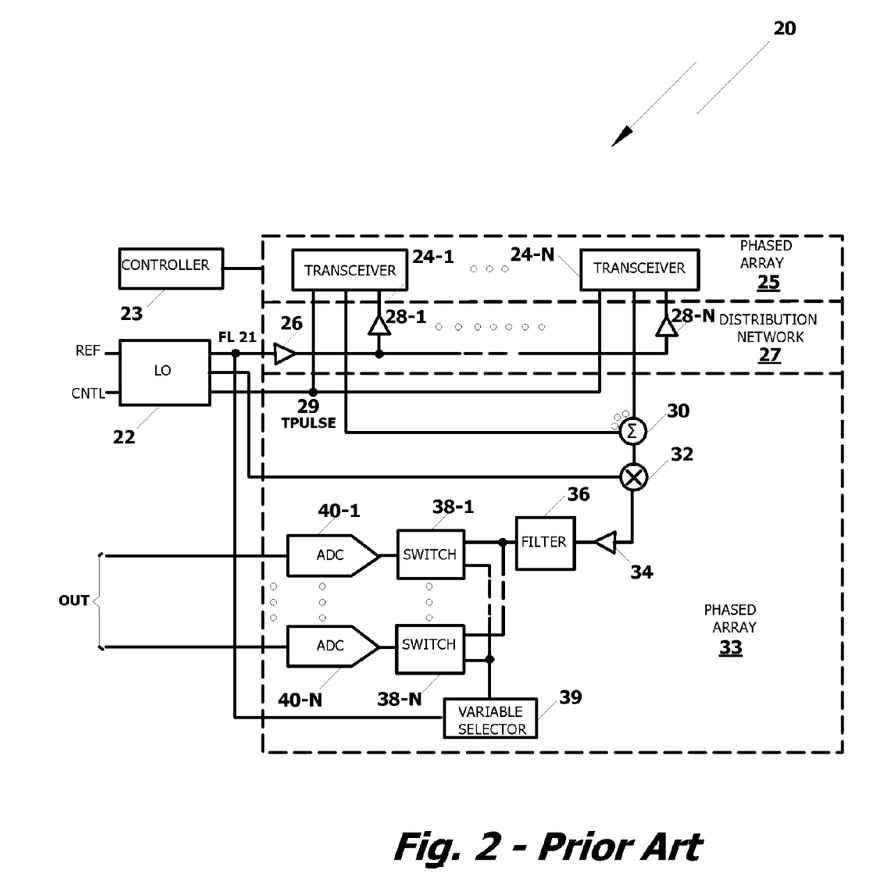
FIG. 2 shows a Phased Array System, according to prior art.

Now referring to FIG. 2, a phased array system 20 is shown. The phase array system 20 generally comprises a Local Oscillator, LO 22, a phased array 25, a distribution network 27, receiver circuitry 33, and controller 23. The phased array 25 generally comprises several transceivers 24-1 to 24-N arranged in an array. The distribution network 27 generally comprises amplifiers 26 and 28-1 to 28-N. Additionally the receiver circuitry generally comprises a summing circuit 30, a mixer 32, amplifier 34, filter 36, switches 38-1 to 38-N, variable selector 39, and Analog-to-Digital converters ADCs 40-1 to 40-N.

Following Ginsburg, in operation, phased array system 20 (which is generally incorporated into an integrated circuit or IC) can generate a short range radar system that operates in the terahertz frequency range (which is generally between 0.1 THz and 10 THz). To accomplish this, local oscillator 22 generates a high frequency signal FL01 that is on the order of tens to hundreds of gigahertz (i.e., 40 GHz, 50 GHz, 67 GHz, and 100 GHz.) and a pulse signal TPUSLE 29. The distribution network 27 then provides signal FL01 21 to each of the transceivers 24-1 to 24-N such that the signals received by each of transceivers 24-1 to 24-N are substantially in-phase. A controller 23 provides a control signal to array 25, which phase-adjusts the transceivers 24-1 to 24-N with respect to one another to direct a beam of terahertz frequency radiation. The transceivers 24-1 to 24-N can then receive reflected radiation back from a target, which is provided to summing circuit 30. The output of summing circuit 30 is the converted to a digital signal by a mixer 32, amplifier 34, filter 36, switches 38-1 to 38-N, variable selector 39, and ADCs 40-1 to 40-N. Additionally, mixer 32 can receive a divided signal from LO 22 (i.e., FL01/2 or another synthesized signal) or can be removed (typically for 40 GHTz or less).

According to Ginsburg, this phased array system 20 generally has several different types of operational modes: pulsed, continuous, and stepped frequency. For a pulsed operational mode, a pulse of terahertz radiation is directed toward a target. The continuous operational mode uses a continuously generated beam, which is generally accomplished by effective "shutting off" the pulse signal TPULSE 29. Finally, stepped frequency allows the frequency of the terahertz beam to be changed, which can be accomplished by employing a bank of local oscillators (i.e., 22). For the pulsed operational mode, in particular, Ginsburg discusses in US Pub. No. 2012/0062286 the range of the system 20 as governed by the following equation:

$$R = \sqrt[4]{\sigma \frac{PG^2 \lambda n E(n)}{(4\pi)^3 kTBF\left(\frac{S}{N}\right)}},$$

for which the various terms are defined in the cited publication and incorporated by reference here.

In contribution to these endeavors, a THz signal generation system is disclosed herein which is based on traveling wave oscillators providing orders of magnitude higher oscillation frequencies resulting in a unique THz transceiver system that can generate, transmit and sense THz frequency signals as described further below in Detailed Description section.

REFERENCES

U.S. Pat. No. 8,130,049 by Huang, et al., teach Generation of Terahertz range (300 GHz to 3 THz). Apparatus and methods describe generating multiple phase signals which are phase-locked at a fundamental frequency, which are then interleaved into an output which is a multiple of the fundamental frequency. By way of example phase generators comprise cross-coupling transistors (e.g., NMOS) and twist coupling transistors (NMOS) for generating a desired number of phase-locked output phases. A rectifying interleaver comprising a transconductance stage and Class B amplifiers provides superimposition of the phases into an output signal. The invention allows frequency output to exceed the maximum frequency of oscillation of a given device technology, such as CMOS in which a 324 GHz VCO in 90 nm digital CMOS with 4 GHz tuning was realized.

U.S. Pat. No. 7,741,921 of Ismailov, et al., describe a Trigger-Mode Distributed Wave Oscillator that provides accurate multiple phases of an oscillation and a method of use of the same. An auxiliary oscillator triggers an oscillation on independent conductor loops or rings forming a differential transmission medium for the oscillation wave. Once the oscillation wave is triggered, the auxiliary oscillator can be powered down to turn it off, and the wave can sustain itself indefinitely through active amplifying devices which can compensate for losses in the conductors.

U.S. Pat. No. 7,550,734 by Lee, et al., shows a heterodyne terahertz transceiver comprising a quantum cascade laser that is integrated on-chip with a Schottky diode mixer. An antenna connected to the Schottky diode receives a terahertz signal. The quantum cascade laser couples terahertz local oscillator power to the Schottky diode to mix with the received terahertz signal to provide an intermediate frequency output signal. The fully integrated transceiver optimizes power efficiency, sensitivity, compactness, and reliability. The transceiver can be used in compact, fieldable systems covering a wide variety of deployable applications not possible with existing technology.

U.S. Pat. No. 7,315,678 of Siegel, et al., pertains to a method and apparatus that provides ultra-low-loss RF waveguide structures targeted between approximately 300 GHz and approximately 30 THz. The RF waveguide includes a hollow core and a flexible honeycomb, periodic-bandgap structure surrounding the hollow core. The flexible honeycomb, periodic-bandgap structure is formed of a plurality of tubes formed of a dielectric material such as of low-loss quartz, polyethylene, or high-resistivity silicon. Using the RF waveguide, a user may attach a terahertz signal source to the waveguide and pass signals through the waveguide, while a terahertz signal receiver receives the signals.

U.S. Pat. No. 6,864,728 by Lu describes a frequency multiplier and amplification circuit. One embodiment of the present invention comprises: a multiplier operably coupled to multiply a first sinusoidal waveform having a first frequency with a second sinusoidal waveform having a second frequency to produce a third sinusoidal waveform, having a frequency representative of a difference between the first frequency and the second frequency, and a fourth sinusoidal waveform having a frequency representative of a sum of the first and second frequencies; and a frequency-tuned load operably coupled to substantially attenuate the third sinusoidal waveform and to substantially pass the fourth sinusoidal waveform as an output of the frequency-tuned multiplier circuit. The frequency-tuned multiplier circuit can be a single-ended multiplier circuit or a differential multiplier circuit with corresponding single-ended or differential first and second sinusoidal waveforms.

U.S. Pat. No. 6,707,344 of Cargill, et al., shows a high efficiency, low noise frequency tripler and method that generates an enhanced third harmonic of a frequency and suppresses the fundamental frequency component in the tripler output. The method comprises multiplying a constant plus a twice frequency component by a square wave at the fundamental frequency, such as by a modulator. The amplitude of the twice frequency component relative to the constant and the phase of the twice frequency component relative to the phase of the square wave are chosen to reduce the fundamental frequency component and enhance the third harmonic in the tripler output. An implementation using a differential Colpitts oscillator is disclosed.

U.S. Pat. No. 5,764,111 by Bushman teaches a voltage controlled ring oscillator integrated with a phase locked loop using CMOS technology. The ring oscillator provides a frequency multiplied harmonic output frequency at a frequency of 2.5 GHz or more while operating at only one-third of that frequency. The ring oscillator uses an odd number of inverter stages and provides high frequency CMOS operation by utilizing the phase shifted signals of the ring frequency at each ring inverter output. The ring oscillator draws minimal current and is incorporated in a frequency synthesizer used in a radio communication device.

U.S. Pat. No. 5,493,719 of Smith, et al., teaches a high frequency receiver which detects and downconverts 50-1,000 GHz radio frequency signals using a receiver consisting of a lens and planar antenna, pre-amplifier, mixer, local oscillator, and IF-amplifier. The insulating dielectric lens is used to focus terahertz radio frequency signals onto the thin film antenna. The preamplifier amplifies these faint signals so that they can be downconverted into an intermediate frequency by the mixer and local oscillator. The mixer is a dual port device which provides isolation of the local oscillator and input signal to avoid saturation of the preamplifier. The IF amplifier boosts the amplitude of the downconverted IF signal produced by the mixer.

U.S. Pat. No. 5,422,613 by Nativ shows an integrated varactor diode frequency multiplier assembly including a first varactor diode frequency multiplier circuit having a non-stepped waveguide output, a second varactor diode frequency multiplier circuit having a non-stepped waveguide input and a non-stepped waveguide for integrally connecting the output of the first circuit to the input of the second circuit, wherein the impedance level of the input of the second circuit is similar to the impedance level of the output of the first circuit.

U.S. Pat. No. 4,400,630 of Owen describes a frequency multiplier using a pair of Schottky diodes to rectify an applied signal, with the rectified waveforms provided by both diodes being combined to produce an output signal having a predominant frequency of twice the applied frequency. In order to prevent distortion occurring at low signal levels, a d.c. bias is applied to the diodes so as to bias them at their threshold values. The effect of temperature variations on the diodes is minimized by using a further diode to determine the effective value of the bias voltage.

U.S. Pat. No. 4,052,673 by Herzog teaches a voltage controlled oscillator which, may be utilized in a phase locked loop, including an odd number (n) of cascaded COS-MOS inverter stages with a feedback path coupling the output of the last stage to the input of the first stage to form a ring configuration. The ring configuration oscillates at a frequency $f_1$ determined by the transconductances of the inverter stages and the shunt capacitances between the stages. Signals comprising impulses of current having frequency components at $f_1$ and $2f_1$ flow through the power supply inputs of each of the stages as they successively are switched from one state to another. A frequency selective impedance path is coupled between a source of power supply voltage and the power supply inputs of each of the stages to develop a second signal having a frequency $f_2$ equal to a multiple $nf_1$ or $2nf_1$. The voltage applied to the commonly connected power supply inputs may be controlled to control $f_1$ and, consequently, $f_2$.

US Pub. 2012,0075034 of Afshari, et al., describes Doppler-Inspired, High-Frequency Signal Generation and U-Conversion compatible with CMOS technology. A circuit is provided that includes two input signals that can propagate on artificial transmission lines in opposite directions, resembling the relative movement of source and observer in Doppler frequency shift; and an output signal combiner. By controlling the characteristics of the transmission lines and the input signal frequencies, the harmonic generation of active devices is utilized and combined to provide the desired high-frequency component at the output.

US Pub. 2012,0169427 of Ahmed, et al., shows a Force-Mode Distributed Wave Oscillator (FMDWO) that provides accurate multiple phases of an oscillation, a Force Mode Distributed Wave Antenna as a radiating element, a Force-Mode Distributed Oscillator Amplifier (FMDOA) and an array of amplifiers capable of operating as a beam forming phased-array antenna driver. Two distinct force mode mechanisms, one delay-based and the other geometry-based, utilizing inverter amplifiers, inject an oscillation on independent conductor loops or rings via transmission lines forming a differential transmission medium for the oscillation wave. Once the oscillation wave is initiated through the forcing mechanisms, the oscillations continue uninterrupted independent of any external triggering.

US Pub. 2008,0169859 by Garcia, et al., teaches a Drain-Pumped Sub-Harmonic Mixer for Millimeter Wave Applications which includes a first transistor having a source and a drain and a second transistor having a source connected to the source of the first transistor and a drain connected to the drain of the first transistor. A mixing transistor is configured to be biased in a linear operating region. The mixing transistor includes a drain coupled to the sources of the first transistor and the second transistor. The mixing transistor has its drain driven by a signal at twice a local oscillator (LO) frequency and its gate driven by a radio frequency (RF) signal while the mixing transistor is biased in the linear region such that a process of frequency doubling and mixing are performed simultaneously.

US Pub. 2008,0137093 of Knag, et al., describes an apparatus and method for generating a terahertz (THz) wave. The apparatus comprises: a fiber optic probe injecting an optical wave transmitted through an optical fiber into a device under test (DUT); a driving oscillator generating and injecting an electrical wave into the DUT; and the device under test (DUT) generating a THz wave using the produced optical and electrical waves.

US Pub. 2006,0016997 of Siegel, et al., presents a sub-millimeter wave frequency heterodyne imaging systems. More specifically, the present invention relates to a sub-millimeter wave frequency heterodyne detector system for imaging the magnitude and phase of transmitted power through or reflected power off of mechanically scanned samples at sub-millimeter wave frequencies.

SUMMARY

TeraHertz radiation is non-ionizing and can penetrate non-conducting materials; hence not harmful to human beings. Its potential uses range from, for example, tomography to outer space communications to airport security to quality control on the manufacturing floor. However, technology for generating and manipulating THz is still in its infancy. In advancement of the THz technology, it is disclosed herein a Traveling Wave Based THz Signal Generation System [TWSGS] and uses Thereof.

Aspects disclosed herein include a Traveling-Wave Frequency-Shift Reflectometer [TWFSR] capable of generating THz signals comprising; a pair of symmetrical Traveling-Wave Frequency Multipliers [TWFM]s as signal sources further comprising; two or more independent electrical conductors forming transmission line loops of a differential medium for traveling wave oscillations; a plurality of cross-coupled inverting amplifiers distributed along said transmission line loops; a plurality of shorted transmission line stubs to provide biasing said cross-coupled amplifiers; a plurality of resistors in series with said transmission line stubs to eliminate low-frequency mode of oscillation; plurality of varactors to provide tuning for high frequency, high-bandwidth oscillations in the range of at least from about sub-GHz to about THz; a coupling for direct coupling said pair of [TWFM]s; and at least a pair of symmetrical supporting back-end devices that form a pair of symmetrical transceivers for simultaneous transmission and reception of THz level signals.

DETAILED DESCRIPTION

In embodiments there is illustrated a Traveling-Wave Based Terahertz (THz) Signal Generation System [TWSGS] for extracting harmonic frequencies from symmetric phases of dual-loop traveling wave oscillators such as TDWO, FMDWO or PDWO cited herein, thereby providing orders of magnitude higher oscillation frequencies than achievable with prior art. The extracted harmonic frequencies from [TWSGS] are further multiplied to higher levels by forming Traveling-Wave based Frequency Multipliers:

[TWFM]: TW-based Traveling Wave Frequency Multiplier

[STWFM]: TW-based Switching Traveling-Wave Frequency Multiplier and using the enhanced multipliers to form transceiver devices, including:

[TWFSR]: TWFM-based Traveling-Wave Frequency-Shift Reflectometer

[TWMR]: STWFM-based Traveling-Wave Modulation Reflectometer

In particular, the recently introduced dual-loop coupled traveling-wave oscillator systems of WaveWorks Inc., such as Trigger-Mode Distributed Wave Oscillators (TMDWO), Force-Mode Distributed Wave Oscillators (FMDWO) and Pumped-Distributed Wave Oscillators (PDWO) provide very accurate multiple oscillation phases. The cited traveling-wave based oscillators generally have—as described in more detail further below—two or more independent electrical conductors forming transmission line loops of a differential medium for traveling wave oscillations; a plurality of cross-coupled inverting amplifiers distributed along said transmission line loops; a plurality of shorted transmission line stubs to provide biasing said cross-coupled amplifiers; a plurality of resistors in series with said transmission line stubs to eliminate low-frequency mode of oscillation; plurality of varactors to provide tuning for high frequency, high-bandwidth oscillations in the range of at least from about sub-GHz to about THz;

In other words, traveling wave oscillators can provide multiple phases with very high frequencies. In contrast, with some oscillators such as the ring oscillators, it is not possible to achieve multiple phases with very high frequencies because the number of oscillation phases is proportional to the number of delay elements (such as inverters) while the oscillation frequencies are inversely proportional to the number of delay elements. Thus, having one type of characteristics denies the availability of the other characteristic. This contradictory condition of multi-phase capability versus the highest achievable frequency does not exist with transmission line based traveling wave oscillators since—at least theoretically—infinite number of oscillation phases are readily available along the traveling wave transmission line tracks. Moreover, recognizing that transmission line and ring type oscillators as analogous to common circuit elements similar to resistors and capacitors, traveling wave based oscillators having distributed capacitive loading can provide a much higher fundamental oscillation frequency compared to lumped or ring-type oscillators.

Figure 3:
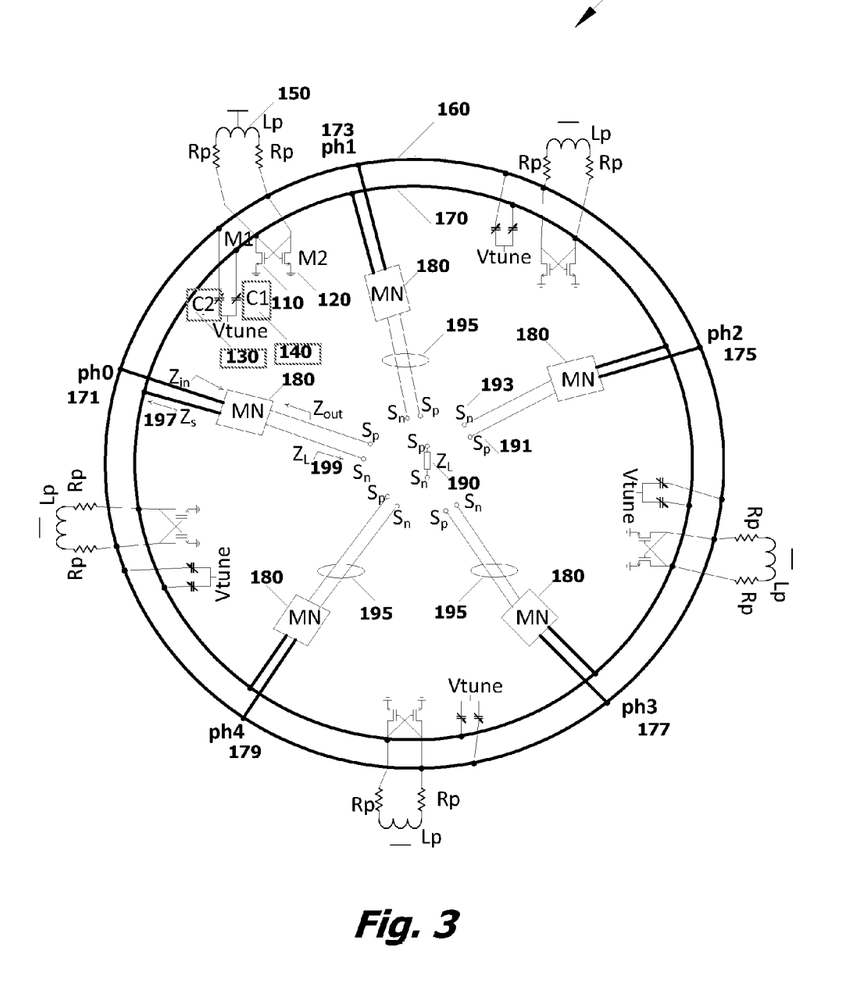
FIG. 3 shows the presently disclosed Traveling Wave Harmonic Extraction scheme with a Pumped Distributed Wave Oscillator (PDWO).

Referring now to the drawings, FIG. 3 is illustrative of Traveling Wave Based Terahertz (THz) Signal Generation System [TWSGS] 100. (Elements drawn similar are not all marked with similar reference numerals in order not to clutter the drawings unnecessarily). The [TWSGS] 100 shown in FIG. 3 extracts the desired harmonic oscillations by incorporating distributed cross-coupled active amplifying devices M1, 110 and M2 120, distributed frequency tuning varactors C1 140, and C2 130, distributed lump inductors Lp 150, and the differential traveling-wave oscillation tracks 160 and 170, and tapping symmetrically at five locations ph0 171, ph1 173, ph2 175, ph3 177, ph4 179 corresponding to the five phases of the traveling wave. These five symmetric phases are combined through a selective matching network MN 180 that drives the desired load 190. It will be known to those skilled in the art that when summed together, the first, the second, the third, and the fourth harmonics of the signal cancel out as depicted in the following equations, whereas the fifth harmonic of the traveling wave signal all add-up since they would all be in-phase at every fifth symmetric tap location. The equations below illustrate the case shown in FIG. 3.

The fundamental frequency content at location ph0 171 is governed by the relationship:

$$ph0(t)=A\cos(\omega t+0\times 2\pi/5)$$

at location ph1 173:

$$ph1(t)=A\cos(\omega t+1\times 2\pi/5)$$

at location ph2 175:

$$ph2(t)=A\cos(\omega t+2\times 2\pi/5)$$

at location ph3 177:

$$ph3(t)=A\cos(\omega t+3\times 2\pi/5)$$

at location ph4 179:

$$ph4(t)=A\cos(\omega t+4\times 2\pi/5).$$

In another aspect, the equal amplitudes of 5 signals with equally spaced phases add up to zero in the exemplary illustration shown in FIG. 3, and consequently combining the signals at the five symmetric tap points, namely, ph0 171, ph1 173, ph2 175, ph3 177 and ph4 179 yield no fundamental frequency signal content. The second, the third, and the fourth harmonic content of the signal bear similar phase relationship resulting in complete cancellation at the center summing nodes, $S_p$ 191 and $S_n$ 193. The fifth order harmonic contents at these tap locations 171, 173, 175, 175, and 179, however, would all be in phase since they repeat at every one fifth distance along the line tracks 160, 170 and add up at the summing nodes $S_p$ 191, and $S_n$ 193. The equations below illustrate this phase relation for the fifth order signal content.

The fifth order harmonic content at location ph0 171 is governed by the relationship:

$$ph0_{5th}(t)=A\cos(5\cdot(\omega t+0\times 2\pi/5))=A\cos(5\omega t)$$

at location ph1 173:

$$ph1_{5th}(t)=A\cos(5\cdot(\omega t+1\times 2\pi/5))=A\cos(5\omega t+2\pi)$$

at location ph2 175:

$$ph2_{5th}(t)=A\cos(5\cdot(\omega t+2\times 2\pi/5))=A\cos(5\omega t+4\pi)$$

at location ph3 177:

$$ph3_{5th}(t)=A\cos(5\cdot(\omega t+3\times 2\pi/5))=A\cos(5\omega t+6\pi)$$

at location ph4 179:

$$ph4_{5th}(t)=A\cos(5\cdot(\omega t+4\times 2\pi/5))=A\cos(5\omega t+8\pi)$$

It will be appreciated by those skilled in the art that the frequency multiplication by five (5) in the exemplary system shown in FIG. 3 can be implemented for any other desired multiplication factor of N by tapping any of the traveling wave based oscillators of Trigger-Mode Distributed Wave Oscillators (TMDWO), Force-Mode Distributed Wave Oscillators (FMDWO) and Pumped-Distributed Wave Oscillators (PDWO) at N symmetric tap points of ph0, ph1, ph3 . . . phN to yield $N^{th}$ order harmonic content. For example, the present disclosure can enable the tapping of a 100-GHz traveling wave based TMDWO, FMDWO and PDWO oscillator at 15 symmetric points from which to extract $15^{th}$ order harmonic content through 15 symmetric paths to generate 1.5 THz signal. In still another aspect of the present disclosure, this multiplicative effect can be made even more efficient by introducing a selective matching network along the harmonic drainage paths 195 from the tap points ph0 171, ph1 173, ph2 175, ph3 177, ph4 179 towards the load center at $Z_L$ 190. Each of these paths 195 displays high impedance of the fundamental frequency not to load the oscillator whereas it matches the oscillator source impedance $Z_S$ 197 to the load impedance 199 at the desired harmonic frequency to be able to transfer maximum harmonic content to the load at 190.

Figure 4:
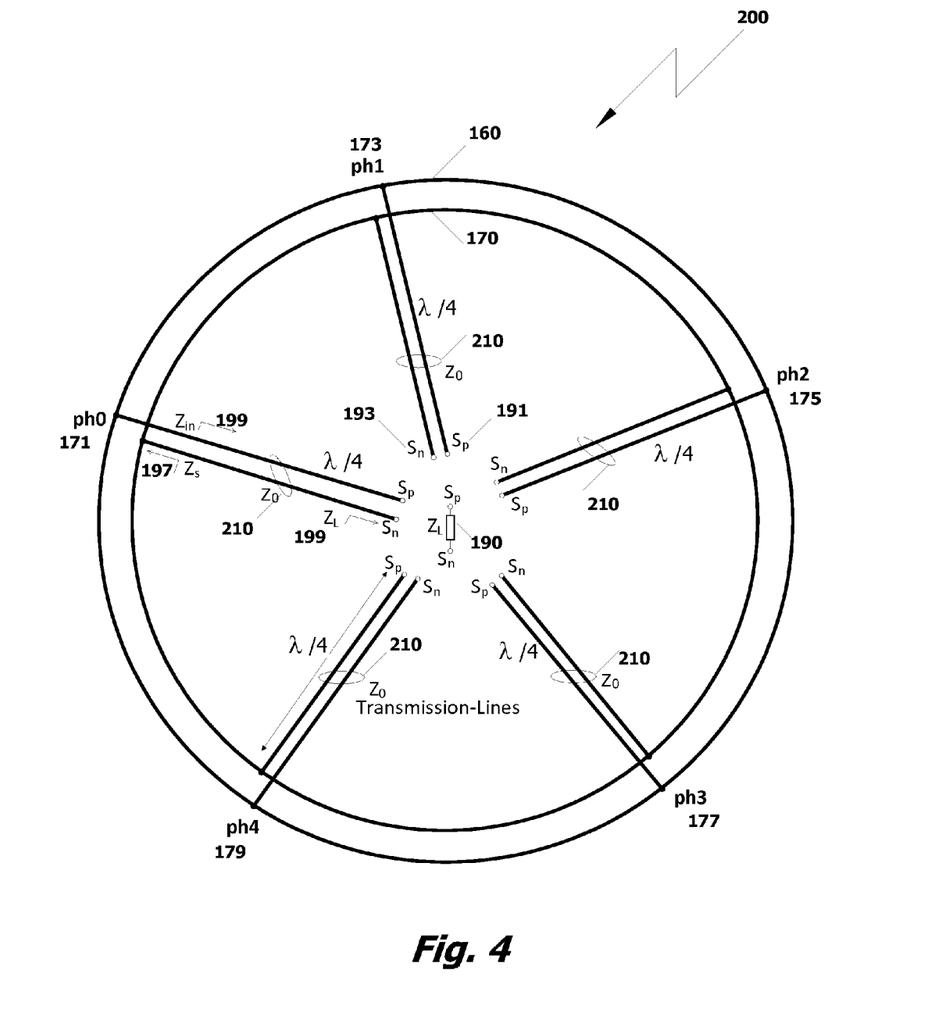
FIG. 4 shows λ/4 transmission-line based harmonic matching and combining network in the presently disclosed Traveling Wave Frequency Multiplier [TWFM].

In yet another aspect of the present disclosure, frequency multiplication can be achieved with selective power combining as shown in FIG. 4. It will be noted that FIG. 4 is a redrawn FIG. 3 where the matching elements in the frequency combining network MN 180 are re-configured to be quarter-wave transmission lines 210 of the fundamental frequency ($\lambda/4$), which is also equivalent to a quarter-wave length for the $5^{th}$-order harmonic signal as shown below;

$$\frac{\lambda}{4} - \lambda_{5th} = \frac{\lambda}{4} - \frac{\lambda}{5} = \frac{\lambda}{20} = \frac{\lambda_{5th}}{4}$$

Generalizing this relation to any odd harmonic content with order 2k+1;

$$\frac{\lambda}{4} - \lambda_{(2k+1)th} = \frac{\lambda}{4} - \frac{\lambda}{2k+1}$$
$$= \frac{\lambda(2k-4+1)}{4 \cdot (2k+1)}$$
$$= \frac{2t \cdot (\lambda_{(2k+1)th})}{4} + \frac{\lambda_{(2k+1)th}}{4}$$

where, $t = k - 1$.

From the above equations, it follows that a quarter-wave length at fundamental frequency does also correspond to a quarter-wave equivalent of all of the odd order harmonics. Referring back to the power/frequency combining scheme of FIG. 4, since the signal summing points [Sp 191, Sn 193] are virtual ground for the fundamental frequency signal, the quarter-wave length stub will transform this virtually zero impedance to ideally infinite impedance ($Z_{in}$ 199=∞ at fundamental frequency) at the tap points ph0 171, ph1 173, ph2 175, ph3 177 and ph4 179. Hence, ideally this harmonic extraction/drainage network will not load the oscillator at its fundamental operating frequency. With respect to the desired harmonic frequency content however, choosing the corresponding characteristic impedance $Z_0$ for the combiner stub 210, [please show where the combiner stub is in FIG. 4. STUB is the combining transmission lines 210] the quarter wavelength can transform a given load impedance $Z_L$ 199' to a $Z_{in}$ 199 value, matching to the source impedance of the oscillator $Z_S$ 197.

$$Z_{in} = Z_s = \frac{Z_0^2}{Z_L}$$

It will be appreciated that the system shown in FIG. 4, hereafter referred to as Traveling Wave Frequency Multiplier [TWFM], provides a capability that does cancel out the fundamental frequency without loading the oscillator at this frequency, while it transfers the maximum power to the load at the desired harmonic frequency. Also, the quarter wave (λ/4) matching and frequency combining provides frequency selective matching for [TWFM]s. [TWFM]s can be used to advantage in custom-tailoring a desired frequency in the THz range as illustrated in FIG. 5.

Figure 5:
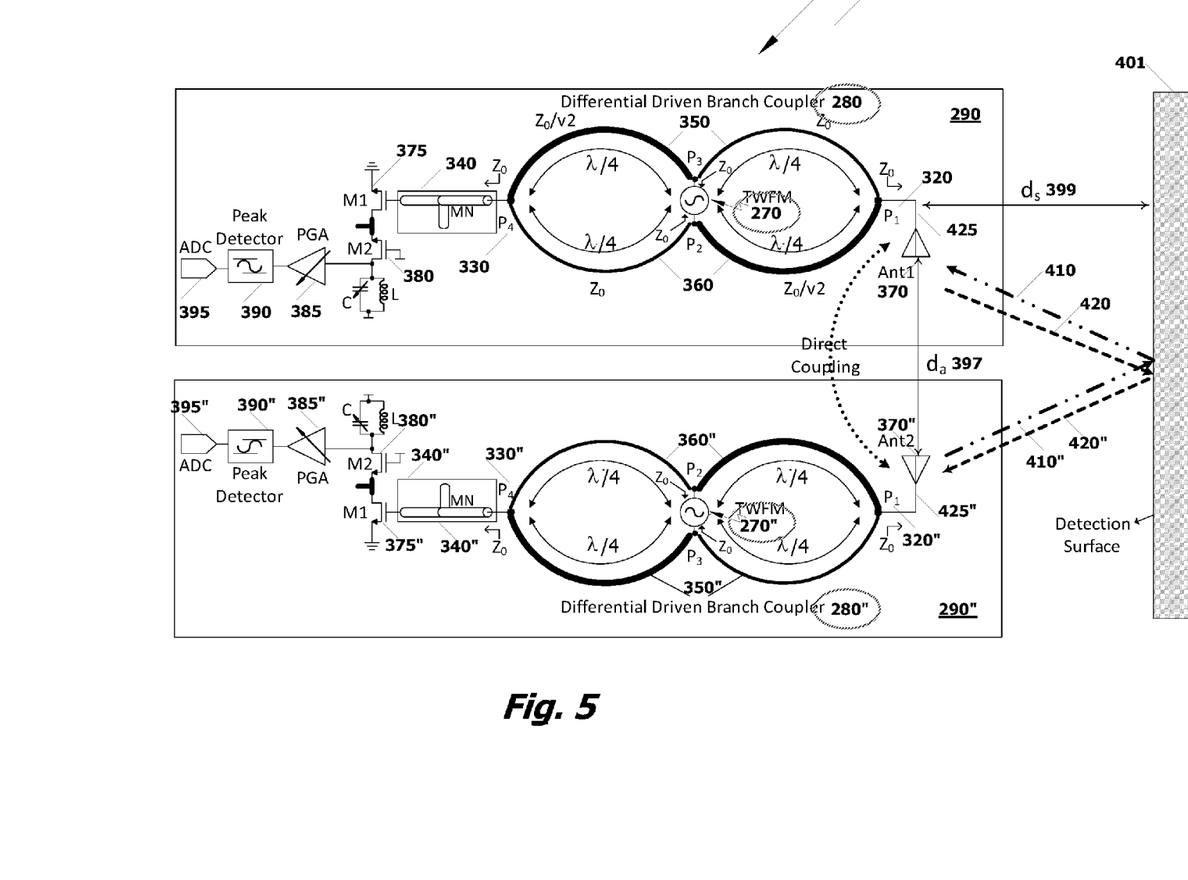
FIG. 5 shows a presently disclosed [TWFM]-based Traveling-Wave Frequency-Shift Reflectometer [TWFSR] transceiver element.

FIG. 5 shows two identical [TWFM]s 270 and 270" coupled together to illustrate a method of targeting a custom-tailored Intermediate Frequency (IF) frequency. The method involves introducing two identical transceivers 290 and 290" which can transmit and receive simultaneously. To achieve a targeted IF, transceivers 290 and 290" are configured to have programmable frequency tuning at each of the oscillators within [TWFM]s 270 and 270" in such a way that the program offsets the frequency accordingly. For example, if the Transceiver 290 TWFM is set to generate 300-GHz tone then the other Transceiver TWFM 290" can be tuned to 297 GHz or 303 GHz resulting in intermediate frequency, IF, frequency of 3-GHz. It will be appreciated that the desired IF-frequency parameter can be incorporated into the design commensurate with the design specifications for a given technology and application thereof. In other words, the two [TWFM]s 270 and 270" can be tuned to the desired offset frequency very accurately during production programming. It will also be appreciated that since these Traveling Wave Frequency Multiplier devices are identical, their frequency drift behavior as a function of environmental factors, such as temperature, humidity, etc., would track each other to a first order, keeping the generation of the intermediate frequency (IF) substantially constant.

It is further disclosed in FIG. 5 that the phase shifting characteristics of Traveling Wave Frequency Multiplier devices may be combined to affect frequency shift thereby enabling their use as a TWFM based Traveling-Wave Frequency-Shift Reflectometer [TWFSR] for synthesizing information from a detection surface.

The two [TWFM]s 270 and 270" in FIG. 5 drive two Differential-Drive Branch Couplers (DDBC)s 280 and 280" which enable simultaneous reception and transmission, of a pair of transceivers Transceiver1 290 and 290", respectively, thus forming a Traveling-Wave Frequency-Shift Reflectometer [TWFSR] 300, which are used for synthesizing information arriving from a detection surface 401, such as shown in FIG. 5. Couplers DDBC 280 and 280" are a special form of the standard 4-port branch couplers, where the two symmetric ports are constructed to be physically close so that they can be driven differentially with two opposite oscillation phases. It will be understood that all the ports of DDBC are matched and the splitting line impedances are set accordingly. The DDBC 280 in Transceiver 1 290 directs one-half of the received power at its port $P_1$ 320 (303 GHz following the example above) to port $P_4$ 330, matched input port of the mixing amplifier 340. The half of the TWFM 270 power at port $P_3$ 350 (300 GHz) flows into mixing amplifier port $P_4$ 330, whereas the other half travels to $P_2$ 360 with 180 degrees phase shift, becoming in-phase with the opposite phase oscillation signal at the same port. Similarly, the power of the opposite TWFM 270" phase at $P_2$ 360" as well splits into two; one reaching to the matched antenna 370" as transmit signal while the other half propagates to $P_3$ 350" becoming in phase when reaching this port. It will be understood that with the disclosed Differential Driven Branch Coupling configuration, therefore, the TWFM signal generated at 270" in Transciever1 290" is split efficiently to be received by the mixing amplifier 340" while at the same time transmitted to antenna 370" without disturbing the differential symmetry of [TWFM]s 270 and 270" in their respective transceivers Transciever1 290 and Transceiver2 290" for which similar numerals referring to similar elements are indicated by double quotes (") in FIG. 5.

When the TWFM signals 410 and 410" from transceivers 290 and 290", respectively, are directed at an object such as a detection surface 401 shown in FIG. 5, the returning signals 420 and 420" find a paths 425 and 425" to their respective mixing amplifiers 340 and 340" with substantially a loss of 3-dB after the antenna. Again following the example given previously, the Transceiver1 290 transmits 300-GHz signal 410 and receives 303-GHz signal 420 while Transmitter2 290" transmits 303-GHz signal 420" and receives 300-GHz 410", reflected from the detection surface 401. As a result, there exist 300-GHz and 303-GHz signals at the inputs of both mixing amplifiers 340 and 340", respectively; hence, the Traveling-Wave Frequency-Shift Reflectometer [TWFSR] transceiver 300, which forms the basis for the THz sensing/imaging device disclosed herein.

It will be noted that in another aspect of the present disclosure, the performance of TWFSR is substantially affected by the direct coupling path 397 from one antenna 370 to the other 370" and vice versa. Any signal coupling in this path would effectively reduce the system dynamic range if the amplitude of this coupling is comparable with the signal received through the reflective path. In order to mitigate this affect and enhance the system performance, the gap between the antennas $d_a$ 397 by design is arranged to minimize the antenna to antenna direct coupling. Moreover, the antenna radiation angle is also tuned to yield maximum reflected signal amplitude for a given distance $d_s$ 399 from the disclosed TWFSR device to surface 401 from which measurements are taken.

It will also be noted that the TWFM-based TWFSR 300 shown in FIG. 5 comprises a pair of Transceivers 290 and 290" which are mirror image of each other including the "back-end" of the devices that are symmetrically identical, namely the mixers M1 375 and 375", M2 380 and 380", Programmable Gain Amplifiers (PGAs) 385 and 385", Analog Digital Converters (ADC) 390 and 390" and digitizing (ADC) 395 and 395". For illustrative purposes of the exemplary device shown in FIG. 5, mixers M1 (375 and 375") are MOS devices which in saturation conditions can very effectively mix down and amplify 300-GHz and 303-GHz down to 3-GHz, due to strong square-law characteristics at this operating region. Mixers M2 380 and 380" are cascade devices which improve the reverse isolation as well as the gain at this stage. Following this low-noise mixing-amplifying stage, the signal is passed through chain of Programmable Gain Amplifiers (PGAs) 385 and 385" to boost the received tone level to full range of the Analog to Digital Converter (ADC) 390 and 390". This is followed by a peak detector output of which is digitized through an ADC 395 and 395". The digital data represents the amount of reflection arriving from the detection/sensing surface 401. The gain in the PGA stage can be adjusted to yield best dynamic range for a particular sensing surface.

Figure 6:
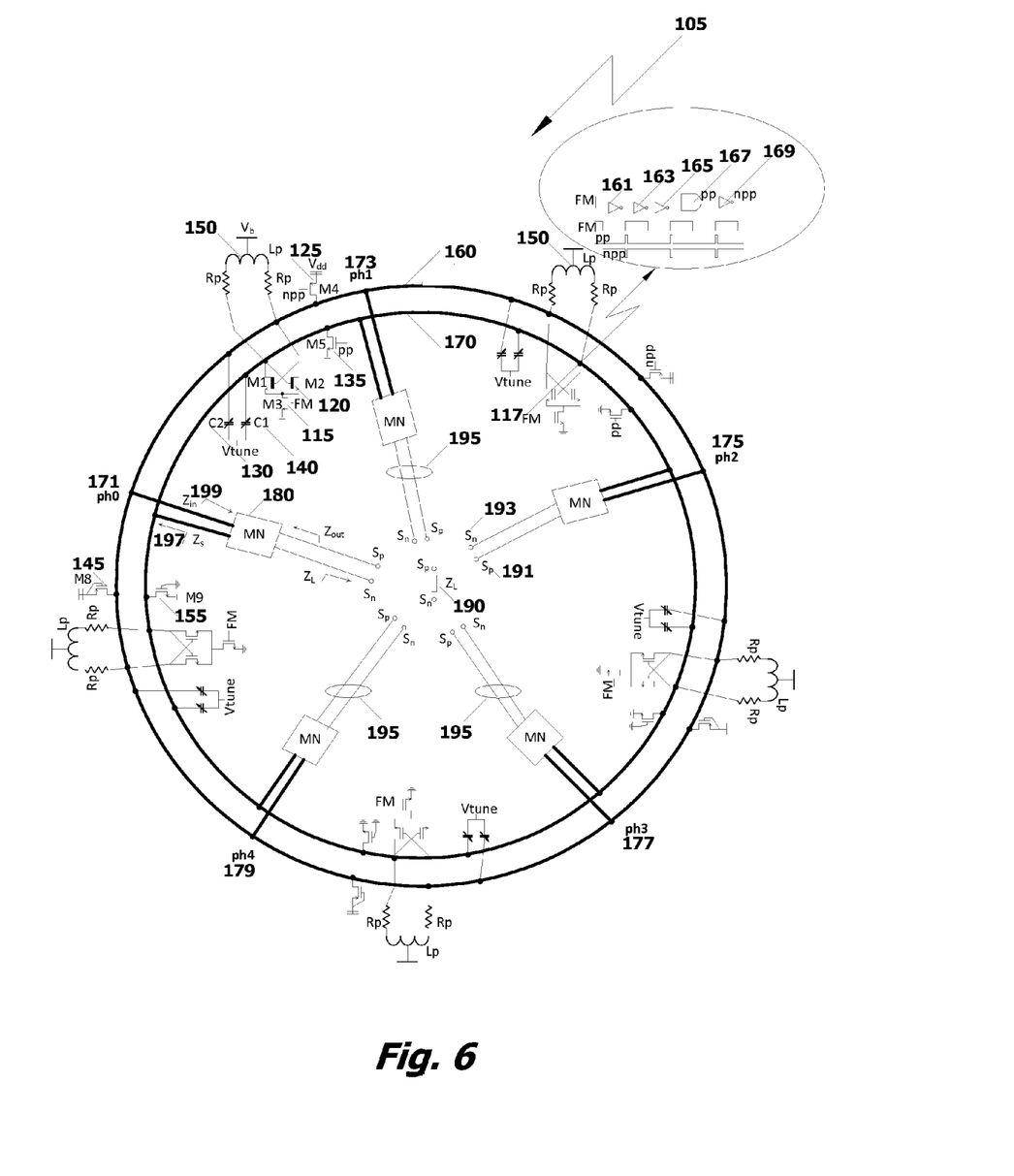
FIG. 6 shows a presently disclosed Switching Traveling-Wave Frequency Multiplier [STWFM] diagram.

A still another type of frequency multiplier, hereinafter referred to as a Switching Traveling Wave-Frequency Multiplier [STWFM] 105 is disclosed in FIG. 6. It will be noted that the STWFM 105 shown in FIG. 6 is derived from TWSGS 100 of FIG. 3, which performs harmonic frequency extraction from symmetric phases of dual-loop traveling wave core oscillators such as TDWO, FMDWO of PDWO referenced previously. In the system shown in FIG. 6, whichever core oscillator is being used is powered on and off using a modulating signal FM at M3 115. It will be observed that when the switching device M3 115 is turned off, the oscillator outputs settle down to a DC bias level Vb 150. When these devices 115 are turned back on again, the oscillation builds up around the same DC operating bias points. In order to speed-up the oscillation build-up the injection devices M4 125 and M5 135 inject narrow opposite pulses, pp and npp into the ring 160 and 170 of the oscillator. These pulses are generated at the rising edge of the modulating clock FM 117. Pulse generating circuits including delay inverters 161, 163, 165 and an AND gate 167 are used to generate narrow pulses driving some of the power-up trigger devices M4 125 and M5 135 on one side of the traveling wave transmission line tracks of 160 and 170 shown in FIG. 6. Additional dummy devices M8 145, M9 155 may also be added as shown in the same FIG. 6 to keep the phases symmetric.

Figure 7:
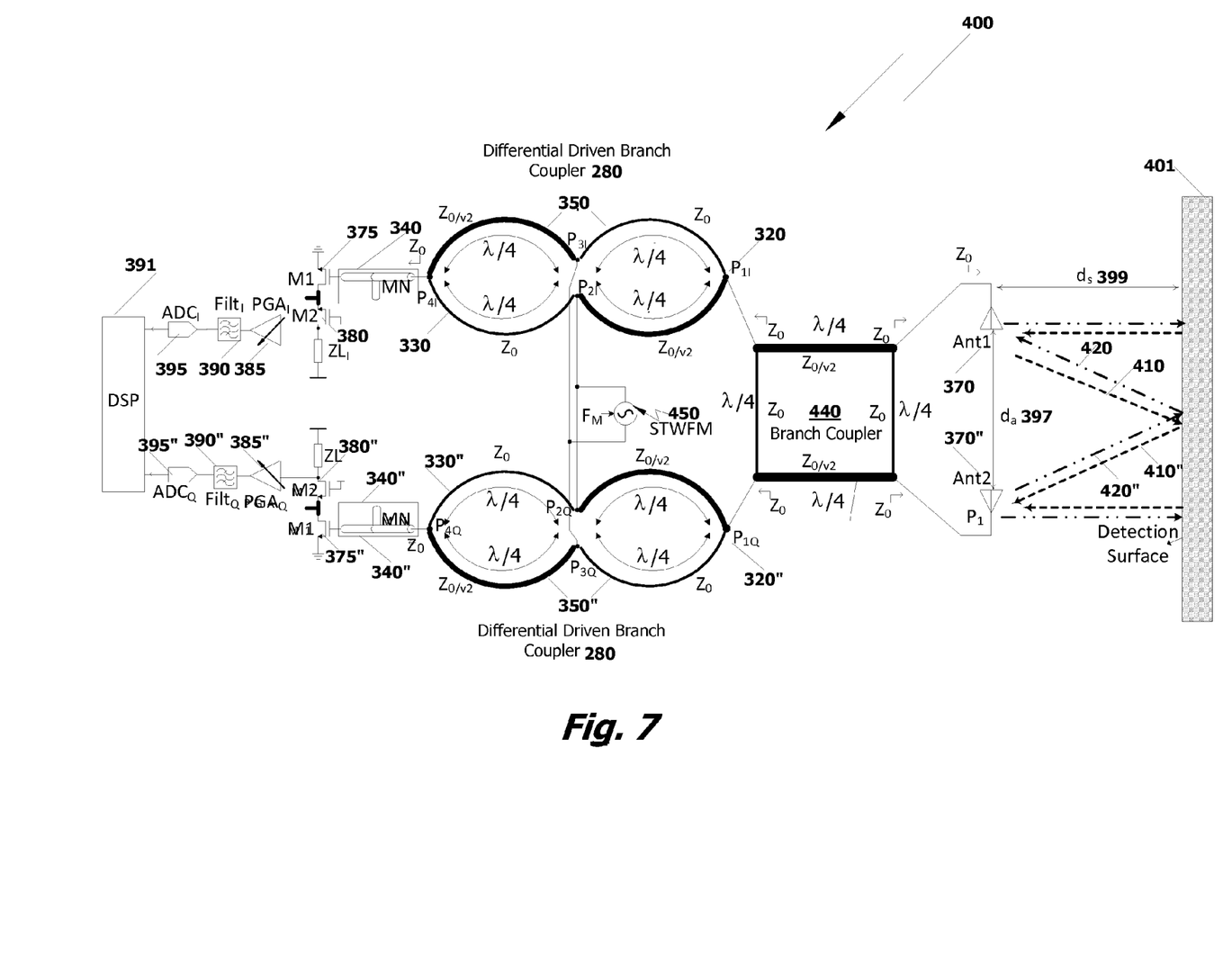
FIG. 7 shows a presently disclosed [STWFM]-based Traveling-Wave Modulation Reflectometer [TWMR] transceiver element.

Using the Switching Traveling Wave-Frequency Multiplier [STWFM] of FIG. 6, the present disclosure introduces another device hereinafter called [STWFM]-based Traveling-Wave Modulation Reflectometer 400, or –[TWMR] for short, as shown in FIG. 7 STWFM 450 of FIG. 7 is used as a signal source to drive symmetrically the Inphase and Quadrature (I/Q) signal paths for direct downconversion of signals of the same frequency reflected from detection surface 401 and traveling with 90 degrees phase shift. (It will be known to those skilled in the art that I/Q data show the changes in magnitude/amplitude and phase of a sine wave. If amplitude and phase changes are made in an orderly, predetermined fashion, one can use these amplitude and phase changes to encode information upon a sine wave, a process known as modulation. Modulation is the process of changing a higher frequency carrier signal in proportion to a lower frequency message (downconversion), or information, signal.)

Referring back to FIG. 7, the reflected signals 420 and 410" that are collected through each of the antennas 370 and 370" pass through symmetrically loaded front-end branch coupler 440 and arrive at I/Q paths 350 and 350" with 90 degrees of phase difference. Signals reaching input ports P1I 320 and P1Q 320" of the differentially driven branch coupler 440 find path to the input matching respective networks 340 and 340" of each corresponding path with a –dB loss (e.g., –3 dB loss of the example given above) along with the same frequency signal generated by the STWFM source 450 into the mixing amplifiers M1 375, M2 380 and M1 375", M2 380". By ON/OFF modulation of the STWFM 450 with a modulation frequency FM, the signal content can be moved to higher frequencies to avoid the impact of DC offset and flicker noise in the final device performance. The downconverted I/Q signals are subsequently amplified [385, 385"], filtered [390, 390"] and finally converted to digital [395, 395"]. The I/Q signals are further processed inside the Digital Signal Processor (DSP) block 391. It will be understood that in the reverse case of signal transmission, the signals coming from the STWFM 450 through both DDBCs [280, 280"] are combined with 90 degrees of phase shift at the front-end coupler 440 feeding the antennas 370 and 370".

Figure 8:
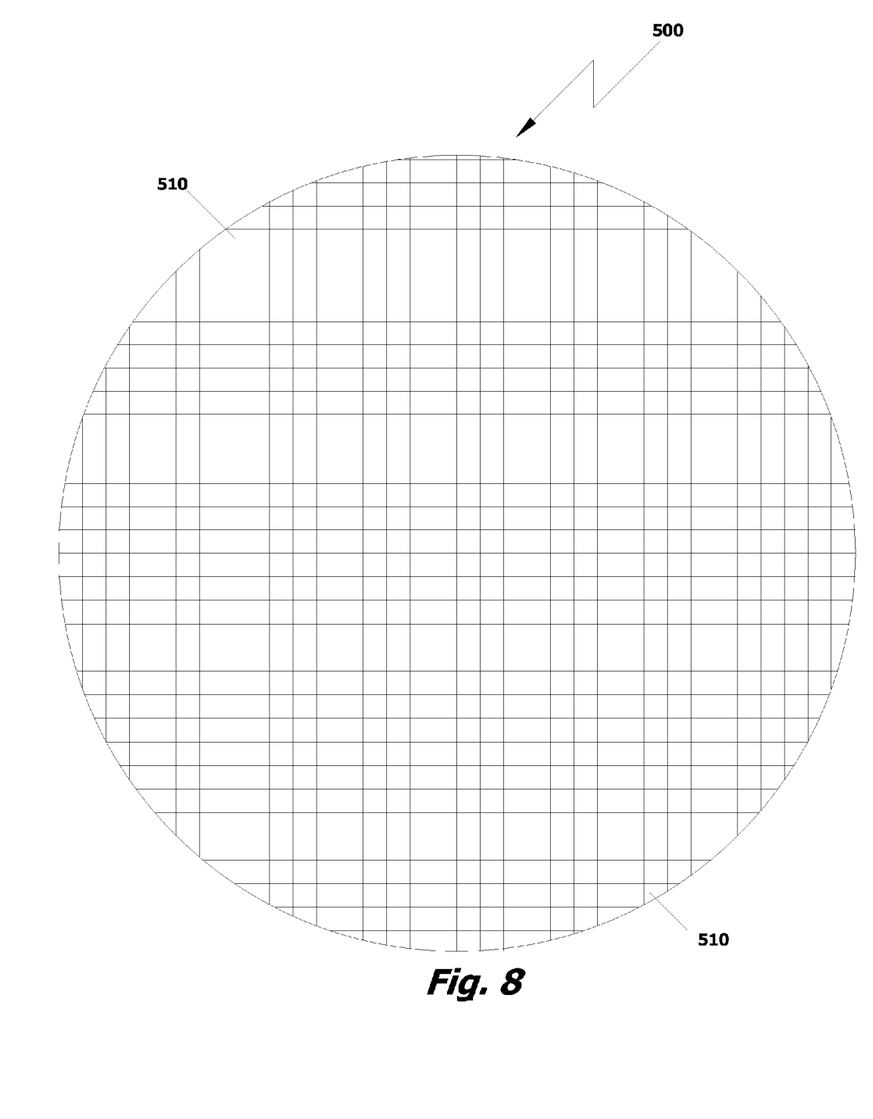
FIG. 8 shows a presently disclosed Wafer-Scale [TWMR/TWFSR] Transceiver Array for THz Sensing/Imaging.

It will be evident to workers in the field that having Traveling Wave-based Frequency-Shift and Wave Modulation Reflectometers [TWFSR and TWMR] of FIG. 5 and FIG. 7, respectively, as disclosed herein can provide the potential use of TeraHertz radiation in areas ranging from tomography to outer space communications to airport security and quality control processes in manufacturing, for example. In this respect, the transceiver elements of FIGS. 5 & 7 are disclosed in an arrangement on a semiconductor wafer as shown in FIG. 8 resulting in a large scale near-field Transceiver Array for THz Sensing & Imaging, 500. In this arrangement, the unit element 510 can be either the [STWFM] or the [TWMR] device depending upon the application used, and propagated across the whole semiconductor wafer.

The device dynamic range of the Transceiver Array 500 can be adjusted by optimizing the gain in the system for a specific sensing application. In operation, the device is first calibrated through a calibration surface similar to detection surface 401 in FIGS. 5 & 7 corresponding to a control surface characteristics of interest. During this calibration scan of the calibration surface, the gain of each unit element across the array is fine tuned to yield uniform clear mid-tone image corresponding to this uniform calibration surface. This way, any mismatches and non-idealities between the unit elements are all calibrated out resulting in a uniform and high accuracy sensing system with high dynamic range. When the real sensing environment applied, the signal received through each element will accurately correspond to the surface characteristics of the environment relative to that of the calibration surface. As an example, if the device is to be used in breast or skin cancer detection, first, an artificial calibration surface corresponding to a healthy breast or skin tissue is used to calibrate all of the array elements across the device to fine accuracy. Subsequently, the device is applied to the patient to get an accurate image of the tissue since any difference from the ideal case will be captured optimally as a result of the initial calibration. The same dynamic range optimization technique can be applied to different calibration surfaces corresponding to different sensing applications. The single device, hence, can serve for multiple THz imaging/sensing applications.

It will be appreciated by those skilled in the art that multiple scanning patterns can be implemented to help construct better image based on the raw data obtained from each of the scan results. For example, in addition to one element at a time sensing method to get density, all of the peripheral elements surrounding the central target in a region can also be activated sequentially along with the center element to obtain more information corresponding to this point of interest. Applying large number of scan patterns and analyzing the data with image construction algorithms, improved image resolution can be achieved.

Further, though these numerous details of the disclosed devices are set forth here to provide an understanding of the present disclosure, it is to be understood that these details of the present disclosure have been described by way of illustration and not limitation. It will be obvious, however, to those skilled in the art that there are other specific details which are inherent in the device, such as, for example, the Traveling-Wave Frequency-Shift Reflectometer [TWFSR] of FIG. 5 may employ, what are known as Wilkinson dividers (see E. J. Wilkinson, "An N-way Power Divider", *IEE Trans. on Microwave Theory and Techniques*, vol. 8, p. 116-118, January 1960) rather than the Differential Drive Branch Couplers (DDBC)s 280 and 280" forming the front-end of [TWFSR] shown in the same FIG. 5. As in the same FIG. 5, two TW-based Traveling Wave Frequency Multipliers [TWFM] 270, 270" are employed, and the direct path from one oscillator 270 to the other 270" is isolated for a matched ideal case. The Wilkinson dividers (not shown) along with mixing amplification devices M1 and M2 find the local oscillation frequency content and additional offset frequency content from the reflected waves. Since in practice the Wilkinson dividers have two symmetric split paths, the mixing devices and number of receive paths can be doubled. When mixed-down with the non-linear square-law amplification action of the active amplification devices M1 and M2, the down-converted signal with frequency content $(\omega_1-\omega_0)$ represents the amount of electromagnetic reflection from the measurement surface. This signal proceeds to subsequent intermediate frequency (IF) tuned low-noise gain chain in the back-end similar to the one in FIG. 5 resulting in digital information corresponding to the received signal level. In practice, there occurs a direct leak from one oscillator to the other side of the Wilkinson branch. In order to account for this error, a calibration step first measures the signal with a nominal uniform calibration surface. The second measurement with the actual surface is compared with the initial reference measurement and the difference represents the target surface characteristics for synthesizing information arriving from detection surface 401 as depicted in FIG. 5.

While the invention has been particularly shown and described with reference to a particular embodiments, it will be appreciated that variations of the above-disclosed embodiments and other features and function, or alternatives thereof, may be desirably combined into many other different systems or applications Also that various presently unforeseen and unanticipated alternatives, modifications, variations or improvements therein may be subsequently made by those skilled in the art which are also intended to be encompassed by the following claims.

What is claimed is:

1. A Traveling-Wave Frequency-Shift Reflectometer [TWFSR] capable of generating THz signals comprising
   a pair of symmetrical Traveling-Wave Frequency Multipliers [TWFM]s as signal sources further comprising
   two or more independent electrical conductors forming transmission line loops of a differential medium for traveling wave oscillations;
   a plurality of cross-coupled inverting amplifiers distributed along said transmission line loops;
   a plurality of shorted transmission line stubs to provide biasing said cross-coupled amplifiers;
   a plurality of resistors in series with said transmission line stubs to eliminate low-frequency mode of oscillation;
   a plurality of varactors to provide tuning for high frequency, and a plurality of symmetric tapping points to tap a plurality of corresponding symmetric phases to affect higher order harmonic frequency extraction to yield high-bandwidth oscillations in the range of at least from about sub-GHz to above THz;
   a coupling for direct coupling said pair of [TWFM]s; and
   at least a pair of symmetrical supporting back-end devices that form a pair of symmetrical transceivers for simultaneous transmission and reception of THz level signals.

2. The TWFSR according to claim 1, wherein said [TWFM] comprises a distributed wave oscillator providing accurate multiple phases of an oscillation for generating THz level frequencies.

3. The TWFSR according to claim 1, wherein said direct coupling comprises a pair of antennas and a pair of differential driven branch couplers for transmitting THz frequency signals.

4. The TWFSR according to claim 1, wherein said supporting back-end devices comprise Mixing amplifiers, Programmable Gain Amplifiers and Analog digital Converters couplers for sensing THz frequency signals.

* * * * *